(12) United States Patent
Palumbo et al.

(10) Patent No.: US 6,398,768 B1
(45) Date of Patent: Jun. 4, 2002

(54) FAECAL COLLECTOR WITH OPTIMALLY SHAPED BAG

(75) Inventors: Gianfranco Palumbo, Bad Homburg; Vincenzo D'Acchioli, Kelkheim am Taunus, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/445,934

(22) PCT Filed: Jun. 26, 1998

(86) PCT No.: PCT/US98/13372

§ 371 (c)(1),
(2), (4) Date: Dec. 20, 1999

(87) PCT Pub. No.: WO99/00092

PCT Pub. Date: Jan. 7, 1999

(30) Foreign Application Priority Data

Jun. 28, 1997 (EP) .............................. 97110602
Jun. 28, 1997 (EP) .............................. 97110603
Jun. 28, 1997 (EP) .............................. 97110604

(51) Int. Cl.[7] .............................................. A61F 5/448
(52) U.S. Cl. ................. 604/355; 604/327; 604/338; 604/339; 604/341; 604/342; 604/385.19
(58) Field of Search .............................. 604/341, 348, 604/331, 337, 385.19, 355, 339, 342, 327, 338

(56) References Cited

U.S. PATENT DOCUMENTS

| | | | | |
|---|---|---|---|---|
| 3,577,989 A | | 5/1971 | Anderson | 128/283 |
| 4,784,656 A | * | 11/1988 | Christian | 604/355 |
| 4,850,986 A | * | 7/1989 | Temple | 604/355 |
| 4,894,058 A | * | 1/1990 | Jensen | 604/332 |
| 5,593,397 A | * | 1/1997 | La Gro | 604/355 |
| 5,961,502 A | * | 10/1999 | Amery | 604/332 |
| 6,206,864 B1 | * | 3/2001 | Kavanaugh et al. | 604/332 |

FOREIGN PATENT DOCUMENTS

| | | |
|---|---|---|
| EP | 0 753 290 A | 1/1997 |
| GB | 1 078 588 A | 8/1967 |
| GB | 1 092 274 A | 11/1967 |
| GB | 2 116 849 A | 10/1983 |
| JP | 08 117261 A | 5/1996 |

* cited by examiner

Primary Examiner—John G. Weiss
Assistant Examiner—Michael Bogart
(74) Attorney, Agent, or Firm—Michael S. Kolodesh; Larry L. Huston; Ken K. Patel

(57) ABSTRACT

A faecal management device. The device has a bag. The bag has an aperture defining a plane and allowing the entry of faecal material. The bag is constructed of two pieces of material joined at a seam, which may lie in a plane parallel that of the aperture. This two-piece construction advantageously allows for a bag geometry which is not long or narrow, thus providing increased comfort for the active wearer.

4 Claims, 7 Drawing Sheets

FAECAL COLLECTOR WITH OPTIMALLY SHAPED BAG

FIELD OF THE INVENTION

The present invention relates to a faecal management device for babies, children or adults to be attached to the perianal area of the wearer, said device having optimum containment properties, i.e., being so configured as to avoid detachment of the bag when the bag contains faecal material, in a wide range of wearing conditions, including situations in which the wearer is not bedridden, but active.

BACKGROUND OF THE INVENTION

Faecal management devices are known articles of manufacture that are designed to be worn principally by incontinence sufferers and in particular by bedridden patients. Such faecal management devices are attached to the perianal region of the wearer and are intended to entrap and immediately contain faecal material and other bodily discharges. Such devices as they are mostly known today are constituted of a relatively long and narrow tube at one extremity of which is positioned the aperture and the attachment device, which can be adhesive.

Because of their shape and dimensions, such devices can twist around the thighs of the wearers and lead to folds and kinks in the devices themselves. Such features naturally affect the storage capacity of the device and may result in unintentional detachment of the device from the wearer leading to undesirable and distressing consequences both for the wearer and carer. Moreover such devices hinder the free movement of the wearer.

Such bags are disclosed in e. g. the following documents:

U.S. Pat. No. 3,577,989, which details a disposable elimination-trapping bag for incontinence sufferers including a container member having an open-top portion, and a flange secured to the container member around the open-top portion. The container member includes two opposed side members, preferably substantially identical, and of a generally rectangular configuration, joined together along common edges. U.S. Pat. No. 4,784,656, which describes a receptacle for collecting faecal matter from incontinence sufferers. The faecal collector comprises a gasket, conduit means or a cylinder and a receptacle; the receptacle and conduit means are each formed from two sheets of thermoplastic film that are heat sealed along their side edges, respectively. GB 2 152 387, which teaches a faecal collector for incontinence sufferers comprising a collection bag and a ring. The faecal collector comprises a pair of panels of thermoplastic sheet material joined at their margins to define an elongate bag having an opening at one end. In a preferred embodiment, the collection bag is formed from a single sheet of odour-barrier thermoplastic film folded along a vertical midline to provide a pair of continuous panels. SE 8 104 934, which discloses an oblong bag made from a thin, flexible and fluid tight material. The collecting bag comprises an inlet portion and a bottom portion at an angle of 120 degrees to the longitudinal direction of the inlet portion. The bag is so designed as to enable it to assume an advantageous position along the thigh of the person when in use.

Other types of faecal management bags of a flatter shape are known from EP 245 064. Such types of flatter bags are also disclosed in U.S. Pat. No. 4,946,720, particularly suited however for collecting faecal matters discharged through the artificial anus. EP 245 064 discloses bags having a front and a rear wall, the front wall containing the aperture and attachment means to the body. The general shape of said front and rear wall is rectangular, i.e., the bag has two opposed long sides and two opposed short sides, the width of the bags being relatively short compared to the length of the bag. Furthermore, the aperture in the front wall is positioned close to one of said short sides of said front wall. Such bags, while improved over the tube-type bags described hereinabove, are still not exhibiting optimum containment properties, especially not in a wide range of wearing conditions.

Hence, a real consumer need can be identified for a faecal management device, which is correctly shaped and dimensioned so as to guarantee the wearer maximum functionality, excellent coverage of the buttocks, and superior comfort.

A problem naturally associated with these devices is their secure attachment to the human body whilst allowing for the faecal matter to be safely contained within the bag. The approach which is mostly used in the field is to provide the device with a flange which surrounds an aperture and provide adhesive on the flange, which will provide sufficient adhesion to the perianal area.

As it is known in the art, the secure adhesive attachment of the faecal management device to allow for a variety of wearing conditions is not easily achieved: The area of the flange is limited, since on the one hand the aperture needs to be of a sufficient size and on the other hand the flange should not be too large for good anatomical fit. Furthermore the adhesive should not be too aggressive in order to avoid pain during the removal of the device.

The wearing conditions will depend on the nature of the wearer; when the wearer is active, such as a baby or a child, or an incontinent adult not being bedridden, the wearing conditions for the bag will become much more stressed and the risk of detachment of the bag will increase substantially, due to the movement of the wearer and pressure from the wearer's body, if the containment properties are not optimum, i.e., there is a likelihood that the faecal material, once excreted and contained in the bag, will exert pressure, in particular onto the inner periphery of the flange, which may result in the unintentional detachment of the bag. Sitting on the bag, for example, will result in a largely reduced volume in some areas of the bag.

Furthermore such pressure exerted by the entrapped faecal material occurring in various wearing conditions may lead to the rupture of the bag, which is an undesirable and distressing consequence, even if only minor leakage of the bag is induced by a rupture. The seals, where different pieces of material used for the bag are joined, e.g. by heat sealing, are typically less resistant to rupture under pressure than other areas of the bag. The weakest areas along such seals are typically bends occurring at the corners of a bag, e.g. when made of essentially rectangular pieces of material as described in the prior art. Bags for faecal management devices are typically made in mass production under economic constraints. Thus a bag having a shape which avoids the need for particularly high quality seals of high economic benefit for the producer and also provides an at least psychological assurance for the user.

It has now been found that the above drawbacks will be substantially alleviated if the bags are configured in a specific manner, thus allowing utilization of the bags for babies, children and active adult incontinents in addition to bedridden adult management device with a specific shape and dimension. It has been found that the resultant faecal management device is uniquely advantageous and exhibits an enhanced level of efficiency and comfort.

It has also been found that the position of the aperture in said specifically configured bags should preferably be selected as well.

In another aspect of the present invention, the faecal management device with its specifically configured shape and dimensions can be advantageously used in combination with a reusable underwear garment or preferably with a disposable diaper.

SUMMARY OF THE INVENTION

The present invention relates to a faecal management device (10) comprising a bag (11), said bag (11) having an aperture (21) and a flange (12) surrounding said aperture for adhesive attachment to perianal of a wearer. The invention resides principally in providing said bag (11) in an optimal shape and with optimal containment properties, so that detachment of the bag is avoided, when the bag contains faecal material, in a wide range of wearing conditions, including situations in which the wearer not bedridden, but active. The present invention relates to a faecal management device for babies, children or adults to be attached to the perianal area of the wearer, said device providing improved anatomical fit and having optimum containment properties, i.e. being so configured as to avoid detachment of the bag when the bag contains faecal material, in a wide range of wearing conditions, including situations in which the wearer is not bedridden but active. Claimed and described is a faecal management device (10) comprising a bag (11), said bag (11) having an aperture (21) and a flange (12) surrounding said aperture (21) for adhesive attachment to perianal area of wearer, said bag (11) having a C1-point and a C2-point, a first distance from the C1-point to the C2-point, a multitude of widths and a maximum width, as defined herein, said bag (1) being characterised in that said first distance is no more that 150% of said maximum width. Said bag (11) furthermore has a multitude of spans and a maximum span and a volume, and is alternatively characterised in that said maximum span is no more than 400% of the cubic root of said volume of said bag (11), preferably said maximum span is no more that 300% more preferably no more that 250% of the cubic root of said volume of said bag (11). Preferred shapes of the bag (11) are according to the present invention a flat circular shape, a cone shape, a truncated cone shape, a pyramidal shape or a truncated pyramidal shape, most preferably a truncated cone shape.

BRIEF DESCRIPTION OF THE DRAWINGS

It is believed that the invention will be better understood from the foregoing description in conjunction with the accompanying drawings in which.

DETAILED DESCRIPTION OF THE INVENTION

Figure 1:
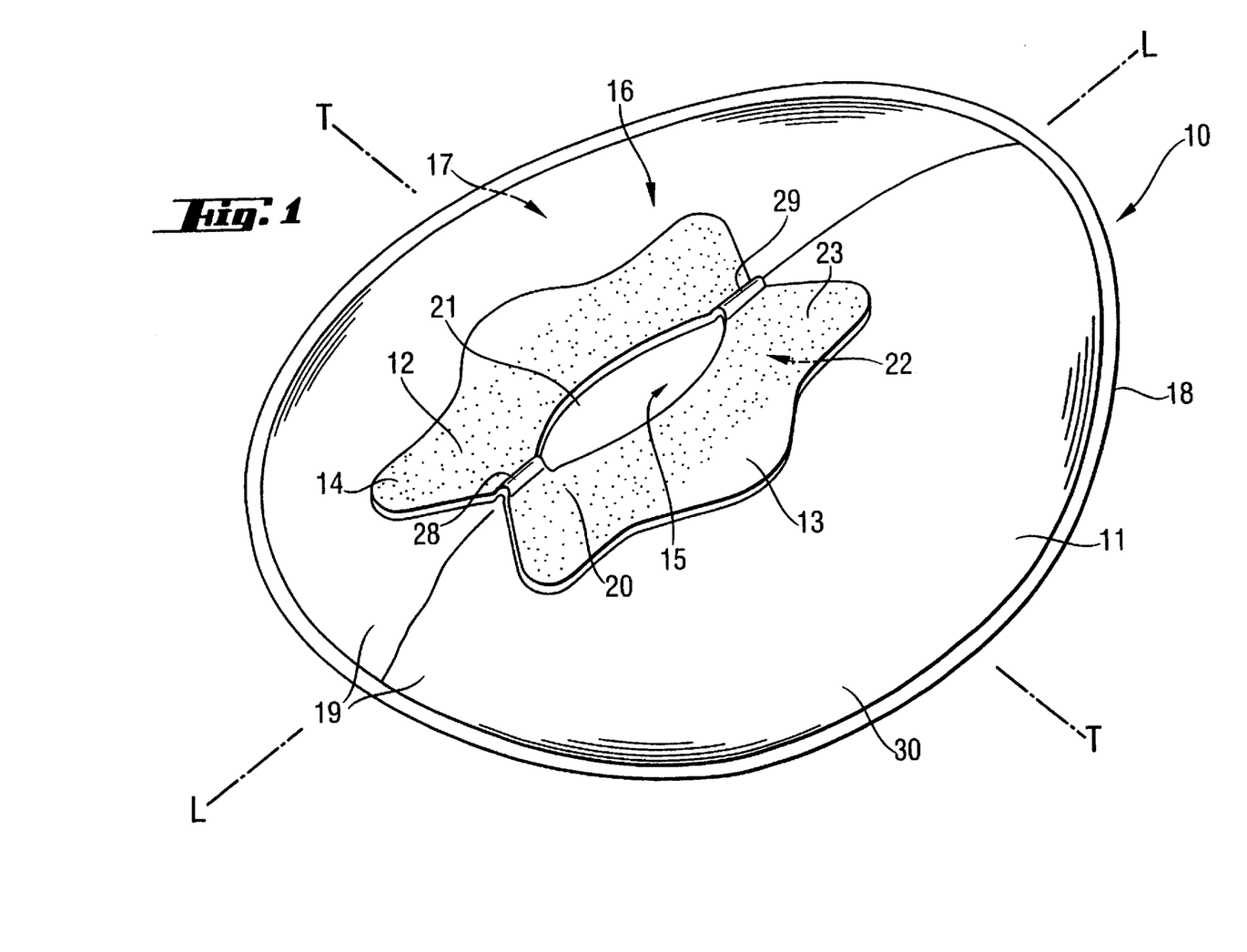
FIG. 1 is a perspective view of a preferred embodiment of the faecal management device.

The invention relates to a faecal management device (10) as shown in FIG. 1. The device (10) comprises a bag (11), which is of particular interest for the present invention.

Description of the Faecal Management Device as a Whole

Typically faecal management devices comprise a bag (11) having an aperture (21) and a flange (12) surrounding the aperture for preferably adhesive attachment to the perianal area of a wearer as visible from FIG. 1. Any faecal management device known in the art can be provided according to the present invention.

The bag (11) as used herein is a flexible receptacle for the containment of excreted faecal matter. The bag (11) is designed to safely contain any entrapped material, typically it will be liquid impermeable, yet it may be breathable. The bag (11) is designed of sufficient strength to withstand rupture in use, also when pressure on the bag (11) is exerted in typical weaning conditions, such as sitting.

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose-wood pulp, cotton, jute, hemp; synthetic fibres such as fibreglass, rayon, polyester, polyolefin, acrylic, polyamid, aramid, potytetrafluroethylene metal, polyimide; binders such as bicomponent high meltlow melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., Ill, U.S. under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film and two non-woven layers. in an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat.

Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner surface (15) of the bag (11). Any known techniques for securing absorbent material to nonwoven and film substrates may be used to secure the absorbent material to the inner surface (15) of the bag. The absorbent material may also be arranged to have any desired shape or configuration (e.g., rectangular, oval, circular, etc.).

As shown in FIG. 1 the bag (11) is provided with an aperture (21) whereby faecal matter is received from the body prior to storage within the bag cavity. The aperture (21) is surrounded by a flange (12) and may be provided in any shape or size, such as circular, oblong, heart shaped and may be symmetrical or asymmetrical, preferably the aperture has an oblong configuration either in the longitudinal: or in the transversal direction or in both directions, e.g., the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering faecal matter.

The flange may be provided in any size depending on the wearer group for which the device is intended. Similarly the flange may be provided in any shape and preferably has a symmetrical shape preferably comprising a plurality of lobes (13)/(14).

The flange comprises a garment facing portion (22) and a wearer facing portion (23). In an preferred embodiment these are two large, substantially flat surfaces, however, the flange (12) may also comprise projections, a front projection (28) and/or a rear projection (29), designed to fit the perineal and/or coccygeal area of the wearer.

The flange (12) should be made of soft, flexible and malleable material to allow easy placement of the flange (12) to the perianal area. Typical materials include nonwoven materials, wovens, open celled thermoplastic foams, closed-cell thermoplastic foams, composites of open celled foams and stretch non-woven, and films. A closed-cell foam of polyethylene has been found effective, but more preferably an open celled polyurethane foam is used. Preferably, such foams have a thickness within the general range of 0.1 to 5 millimeters and a density of 5 to 250 g/m$^2$, more preferably 50 g/m$^2$. Other thermoplastic foam materials, or other suitable plastics sheet materials having the described properties of such foams (i.e., softness, pliability, stretchability, and contractability) might also be used. Preferably, the material of garment facing portion (22) of the flange (12) may extend into the defined aperture area so as to form a skirt or flap of material which prevents unintentional adhesion of the surface edges of the flange (12) defining the aperture (21) to one another during use.

According to the present invention the faecal management device (10) further comprises an attachment means to secure the device to the wearer. Such means include straps and more preferably comprises a body-compatible pressure sensitive adhesive (20) applied to the wearer facing portion (23) of the flange (12).

The adhesive (20) is preferably covered with a release means (not shown) in order to protect the adhesive (20), such as siliconized paper. The adhesive (20) can cover the entire wearer facing portion (23) of the flange (12) or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing portion (23) of the flange (12), so as to provide lobes (13)/(14) on either side of the flange (12) which are non-adhesive and can thereby serve to facilitate placement and removal of the device whilst avoiding contact with the adhesive. These lobes (13)/(14) are however preferably also covered by the release means. Before application of the faecal management device (10) to the skin of the wearer, the release means if present is removed.

According to the present invention any medically approved water resistant pressure sensitive adhesive may be used to attach the device to the perianal area of the wearer, such as hydrocolloid adhesives and hydrogel adhesives.

Particularly effective adhesives in providing the desired adhesive properties to secure the flange to the skin of the wearer at the sensitive perianal area, whilst allowing for relatively painless application and removal, are formed from crosslinking polymers with a plastisicer to form a 3-dimensional matrix.

The adhesive (20) can be applied to the wearer facing portion (23) of the flange (12) by any means known in the art such as slot coating, spiral, or bead application or printing. Typically the adhesive (20) is applied at a basis weight of from 20 g/m$^2$ to 2500 g/m$^2$, more preferably from 500 g/m$^2$ to 2000 g/m$^2$ most preferably from 700 g/m$^2$ to 1500 g/m$^2$ depending on the end use envisioned. For example, for faecal management devices (10) to be used for babies the amount of adhesive (20) may be less than for faecal management devices (10) designed for active adult incontinence sufferers.

Figure 2:
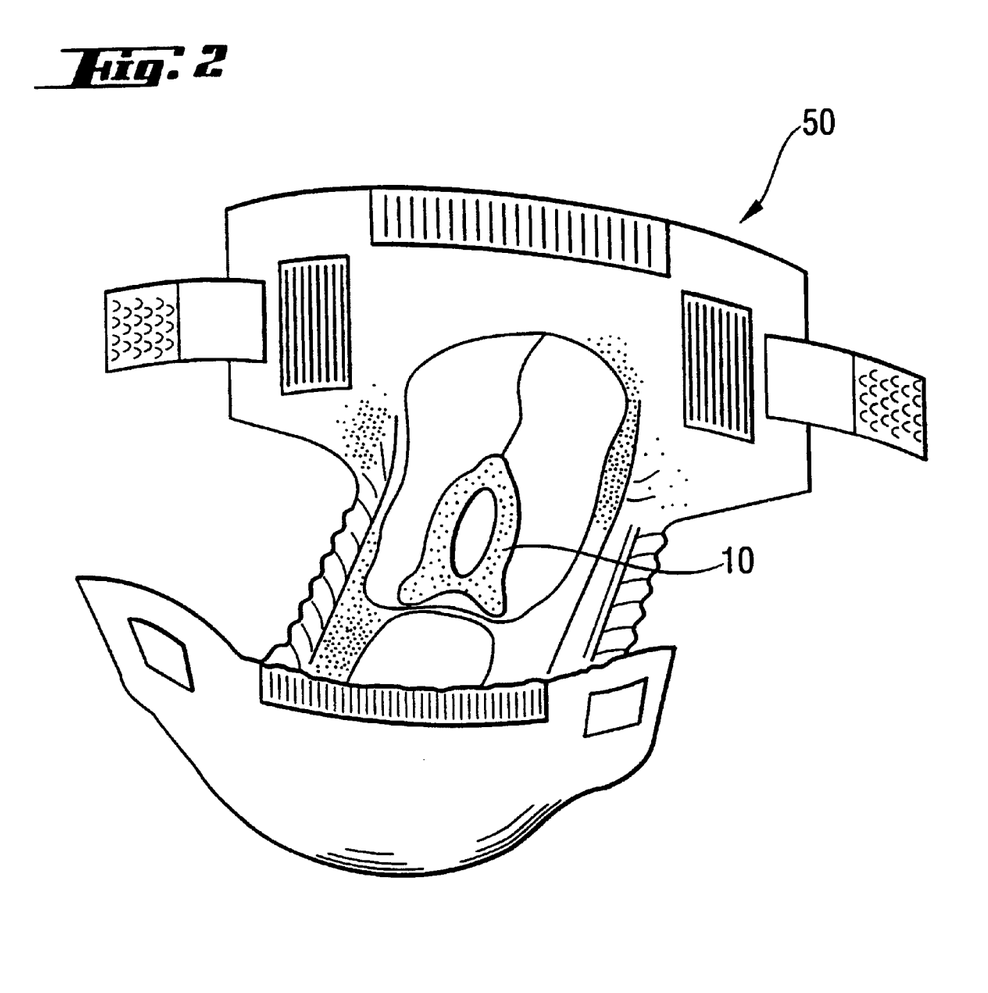
FIG. 2 is a perspective view of a diaper and a faecal management device, which can be worn in combination according to the present invention.

Detailed Description of a Diaper to be Worn in Combination with the Faecal Management Device The faecal management device (10) of the present invention has been found to be particularly useful and beneficial when used in conjunction with a garment, or diaper (50), preferably a disposable diaper—refer to FIG. 2. The faecal management device (10) is preferably first placed in the perianal area of the wearer before the disposable diaper (50) is applied. In particular, the diaper (50) is positioned over the faecal management device (10) and fastened in a conventional manner around the body of the wearer. It has been found that, in addition, to providing excellent separation between urine and faecal material, the combined faecal management device (10) and diaper (50) system actually reduces skin irritation, which may at times occur, especially since the group of typical wearers includes the very old, the very young and the unhealthy wearers. In effect, the presence of the faecal management device (10) permits the formation of a separation layer between the skin of the wearer and the diaper (50), i.e., a part of the absorbent core (58) of the diaper (10). The diaper (50) can be of the conventional type (an embodiment of which is described below although not a limiting example by any means) or can be adapted to contain in an effective and comfortable manner the faecal management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
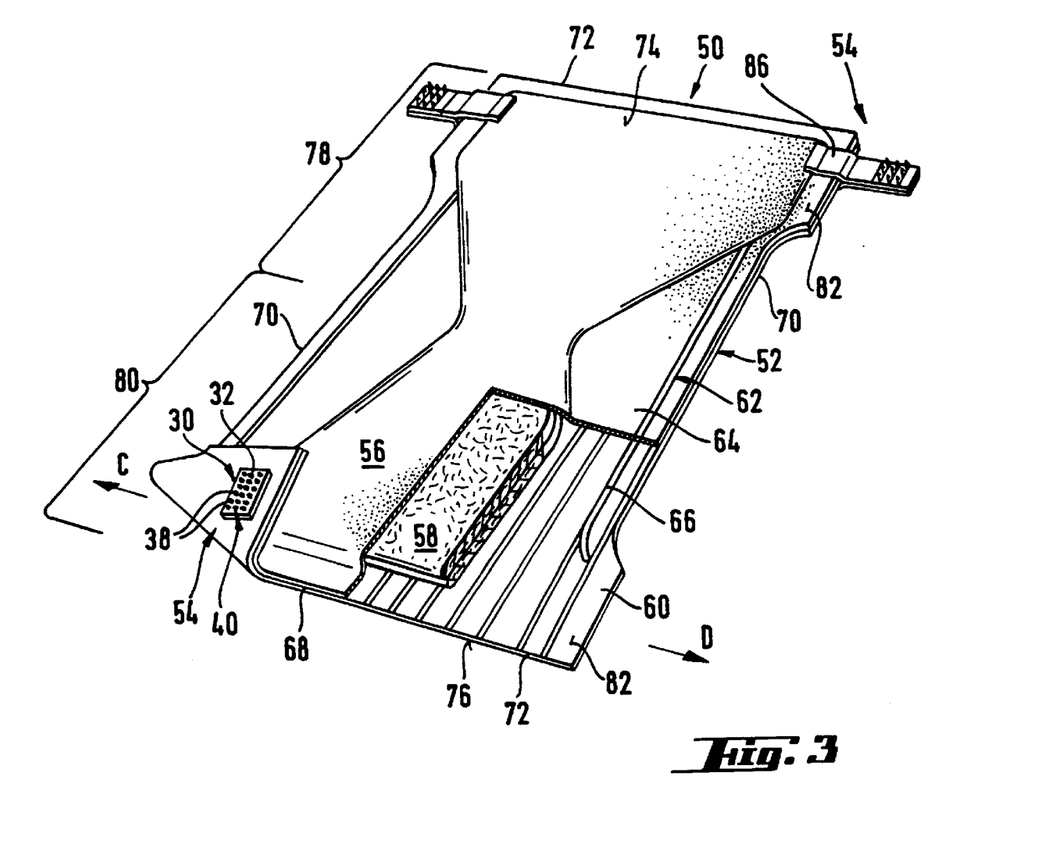
FIG. 3 is a partially cut-away perspective view of a diaper to be worn in combination with a faecal management device according to the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50)

opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying caliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diapers is compliant, soft feeling and non-irritating the skin of the wearer. Further, the topsheet (56) is liquid thus permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combiantion of natural and synthetic fibres. Preferably, it is made of a material that isolates that isolates the skin of the wearer from liquids retained in the sbsorbent core (58).

There are a number of manufacturing techniques which may be used to manufacture the topsheet (56). For example, the topsheet (56) may be a non-woven web of fibres. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

Detailed Description of the Bag

To allow a more detailed and clear description of the shape of the bag (11) of the present invention, in the following paragraphs firstly a number of terms, as used herein, will be defined.

Regarding in particular the flange (12) the longitudinal axis is to be understood as follows: The direction which is substantially defined by the anal groove in the intended wearing position shall define the longitudinal direction. The longitudinal axis is an axis in the longitudinal direction, which crosses the centre of the aperture (21). The most preferred indication of the intended wearing position is the presence of one or two projections (28) and/or (29) designed to fit the perineal or coccygeal area of the wearer, a less preferred indication of the intended wearing position is a fold in said flange (12) prior to use intended to be placed in parallel to the anal groove when placing the product. The longitudinal axis is typically also an axis of symmetry of the bag (11).

The transversal axis is an axis perpendicular to said longitudinal axis, which crosses the centre of the aperture (21). The bag is typically not symmetrical to the transversal axis.

A section of material is to be understood with regard to the bag (11) as a piece of material cut from the material used for the bag (11), which can be laid flat on a even surface and does not comprise any seals or rims. A section of material may comprise separate layers as described above.

The garment facing portion (17) is the portion of the bag (11), which is generally oriented away from the wearer, when the faecal management device (10) is worn, and towards a garment, if a garment is worn. The garment facing portion (17) does not comprise the aperture (21). The size and the shape of the garment facing portion (17), in particular its length and width, are defined by the bag peripheral rim (18). Sections of material comprised by the rim (18) or seal do not form part of the garment facing portion (17).

The wearer facing portion (16) is the portion of the bag (11), which comprises the aperture (21) and is generally oriented towards the wearer, when the faecal management device (10) is worn. The size and the shape of the wearer facing portion (16) are defined by the bag peripheral rim (18). Sections of material comprised by the rim (18) or seal do not form part of the wearer facing portion (16).

The surface area of the garment facing portion (17) and the surface area of the wearer facing portion (16) are the areas of the outer surfaces (30) of said portions. Material comprised by the rim (18) is not to be taken into account.

The term length as used for the length of the garment facing portion (17) refers to the length measured on the garment facing portion of the bag (11) along the longitudinal axis.

The term width as used for the width of the garment facing portion (17) refers to the length measured on the garment facing portion of the bag (11) along the transversal axis.

Centre is used to describe a point of an object or a part of an object, which coincides with the centre of mass, if said object or part were of uniform density. Thus for the aperture (21), the centre is to be determined when the area within the contour of the aperture (21) is considered to be filled with a material of uniform thickness and density, when the flange (12) is unbent.

Unbent is used with regard to the flange (12). The flange (12) is typically bent along a longitudinal axis to place it onto the perianal area of the wearer. In an unbent state the flange (12) is typically flattest.

Flat is used in the description of a three-dimensional object, such as the flange (12), if the object can be thought to be fully contained by a cuboid, characterised by three characterising lengths, of which one first length is less than half of either of the two other characterising lengths. If the object is flexible in shape, so that it may take several shapes without a substantial effect on its properties or damage, it is called flat if it is flat in one of said shapes. Such an flexible object is in its flattest shape if said first characterising length is minimal.

The faecal management device (10) is in the in-use position when the device (10) is attached to the perianal area of the wearer, so that the aperture (21) is registry with the anal opening of the wearer and the flange (12) is typically bent along the longitudinal axis.

The z-axis is an axis which is perpendicular to both the longitudinal and the transversal axis and which crosses the centre of the aperture (21).

The shape of the bag is to understood as the shape exclusively defined by the material forming the bag. While the shape of the bag (11) is thus fully defined by geometrical considerations, the nature of the shape of the bag may be more clearly identified when the bag is inflated with a gas such as air, so that equal pressure is exerted onto the inner layer of the material forming the bag. The pressure should, however, be low enough, so that the material forming the bag is not substantially stretched. Said shape of the bag also determines the volume of the bag.

The C1-point denotes a point on said z-axis which is located at a point 1 cm from said centre of the aperture (21) of the unbent flange (12) towards the point where the z-axis crosses the bag (11). The C1-point approximately describes the centre point of entry of faecal matter into the bag (11) when the faecal management device (10) is in its in-use position. The C2-point denotes the centre of the shape of the bag. The C3-point denotes the point where the c-axis crosses the outer surface (30) of the bag (11).

The c-axis is an axis connecting said C1-point and said C2-point. The direction from the C1-point to the C2-point defines the positive direction on the c-axis.

C1–C2 distance denotes the distance from the C1-point to the C2-point.

The term width, as used herein with regard to the bag (11), defines the width taken from a Cx-point, on the c-axis, along the axis which is perpendicular thereto to the furthest away point where said perpendicular axis crosses said bag's outer surface (30).

The term average width denotes the average of all said widths measured about a given Cx-point on the c-axis.

The term maximum average width denotes the maximum width value from all of said average widths taken at all different Cx-points on the c-axis.

The term overall average width denotes the average of all of said average widths for all Cx-points on said c-axis as defined herein above.

A span, used with regard to the bag (11), is the length measured along any axis which crosses the outer surface (30) of the bag (11) at two points and denotes the length between said two points.

According to the present invention, depending on the shape of the bag (11) required, the bag (11) may be provided from a unitary piece of material or a number of separate pieces of material, which may be identical or different and which are sealed at their respective peripheries. The preferred shape of the bag depends in particular on the intended use thereof, i.e., whether the device is intended for bedridden patients or active patients suffering from incontinence or requiring an artificial bowel or for infants.

In particular if the bag (11) is provided from a unitary piece of material, the shape of the bag (11) may be adapted to conform to the shapes of a bag (11) within the scope of the present invention by techniques known by the man skilled in the art. These techniques include creping, corrugating, ring rolling, or pleating and may be applied to all pieces of material comprised by the bag (11), or only to some pieces or only to certain areas.

The bags described herein preferably have a wearer facing portion (16) and a garment facing portion (17), which both comprise separate pieces of material. The wearer facing portion (16) and the garment facing portion (17) are sealed at the periphery of the bag (11), thus creating a bag peripheral rim (18). The wearer facing portion (16) and the garment facing portion (17) may each independently comprise more than one section of material. FIG. 1 depicts an embodiment, where the wearer facing portion (16) comprises two sections (19). Preferably the garment facing portion (17) comprises only one section of material; most preferably also the wearer facing portion (16) comprises only one section of material, as is visible from FIGS. 4 and 5.

The wearer facing portion (16), the garment facing portion (17) and the pieces of material comprised by either of these portions are secured to each other by means known to the man skilled in the art, such as adhesive, thermobonding or pressure bonding in order to provide the desired bag configuration. The rim (18), at which the wearer facing portion (16) and the garment facing portion (17) are sealed together, may be provided inside the bag (11) rather than outside the bag (11), thus being coextensive with the inner surface (15) of the bag (11) rather than with the outer surface (30) of the bag (11).

According to the present invention it has been found that faecal management devices provide improved containment properties and improved fit and comfort, when the bag (11) is configured as described in the following. In particular it has been identified as an essential feature that the C1–C2-distance should be no more than 150%, preferably no more than 125%, more preferably no more than 115%, more preferably no more than 100% of the maximum width of the bag (11). Preferably the C1–C2-distance is more than 5%, preferably more than 15%, more preferably more than 25% of the maximum width.

More preferably, the C1–C2-distance should also be less than 200%, preferably less than 150% of the maximum average width, more preferably between 100% and 10%, yet more preferably between 80% and 20% of the maximum average width. In an even more preferred embodiment, the C1–C2-distance should be less than 200%, preferably less than 150% of the overall average width, more preferably between 100% and 10%, yet more preferably between 80% and 20% of the overall average width.

Figure 6:
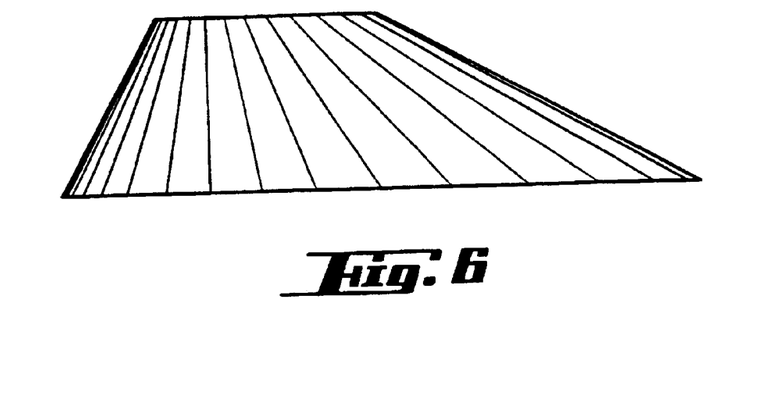
FIG. 6 is a side view onto a bag for a preferred faecal management device in accordance with FIGS. 4 and 5, which illustrates a substantially truncated cone shaped bag.
Figure 7:
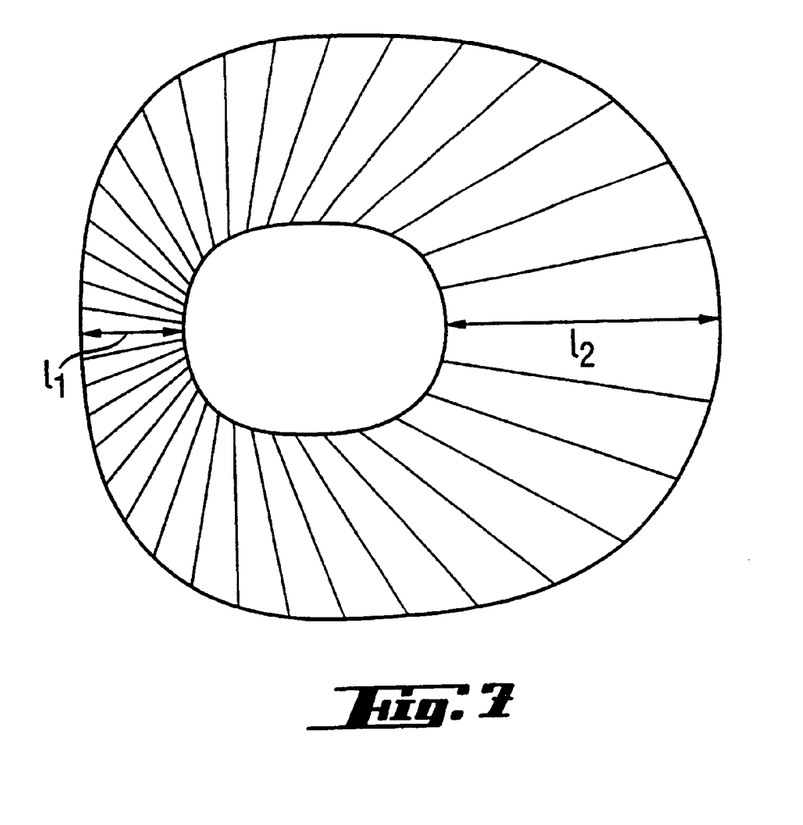
FIG. 7 is a top view onto the wearer facing side and the aperture of a bag of a preferred faecal management device in accordance with FIGS. 4, 5 and 6.
Figure 8:
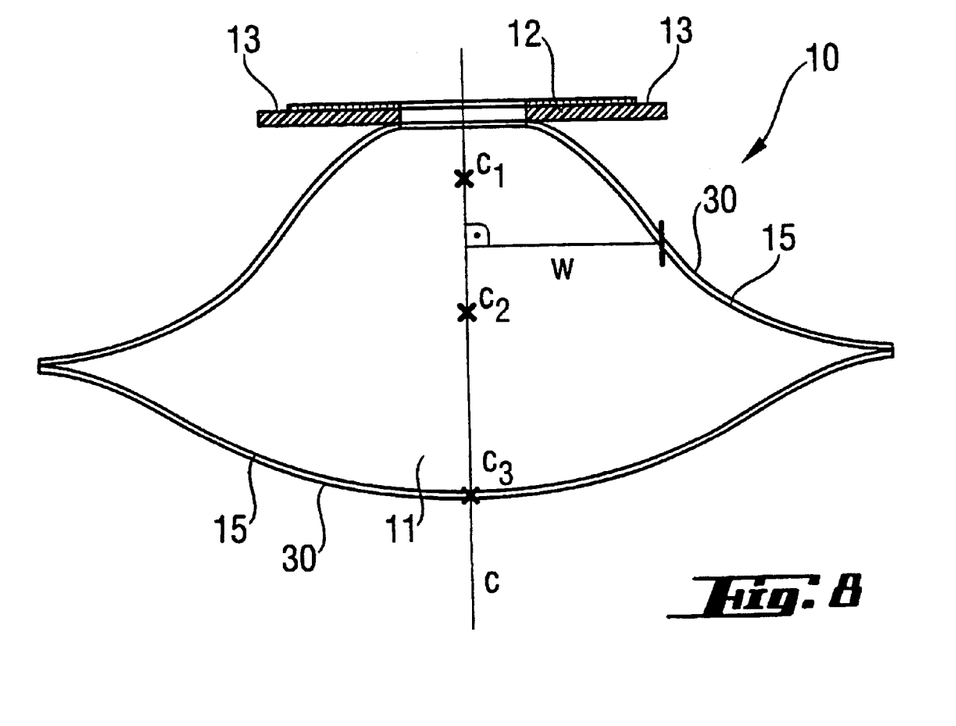
FIG. 8 is a cut-away side view in the transversal direction of a preferred faecal management device. C1, C2 and C3 denote the C1-point, C2-point and C3-point, respectively, c denotes the c-axis and w denotes a width.

Another feature of a preferred embodiment of the present invention is that the bag should be provided so that the average width of the bag (11) is not constant, such that there is a maximum average width and a minimum average width, as can be inferred from FIGS. 6 to 8. Preferably said maximum average width is at least 20%, more preferably at least 50% greater than said minimum average width. More preferably, the average width increases continuously along the positive direction of the c-axis, over at least 10%, preferably at least 25%, more preferably at least 50% of the length of the c-axis between the C1-point and the C3-point.

Yet another characterising feature of the present invention is that the bag (11) is not of a long or narrow shape, as illustrated e.g., by FIGS. 6 and 7. This is to say, any span of the bag (11) is no more than 400% of the cubic root of the volume of the bag (11). In a more preferred embodiment said span is no more than 300%, preferably no more than 250%, most preferably no more than 200% of the cubic root of the volume of the bag (11).

Figure 4:
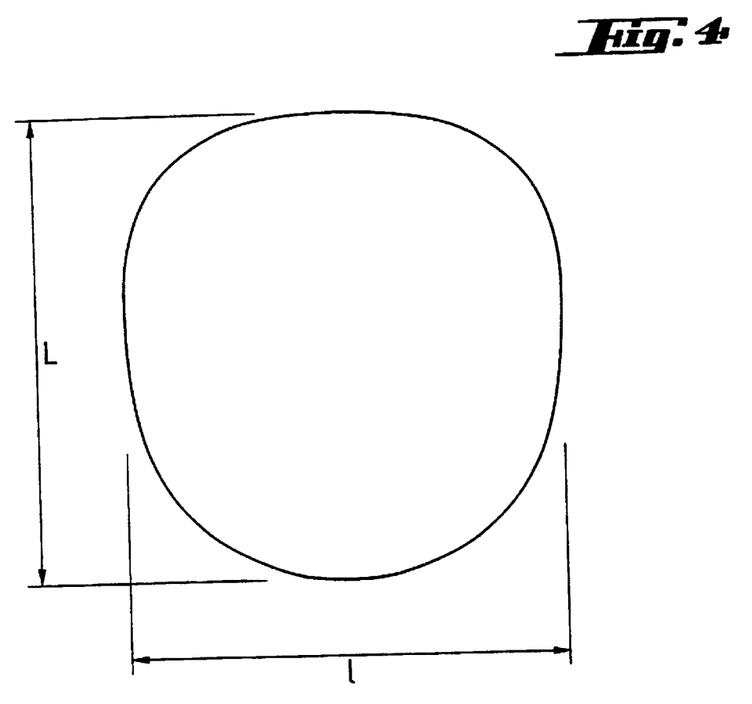
FIG. 4 is a view of the garment facing portion of a preferred faecal management device in which the ratio of length to width is 1:0.92.
Figure 5:
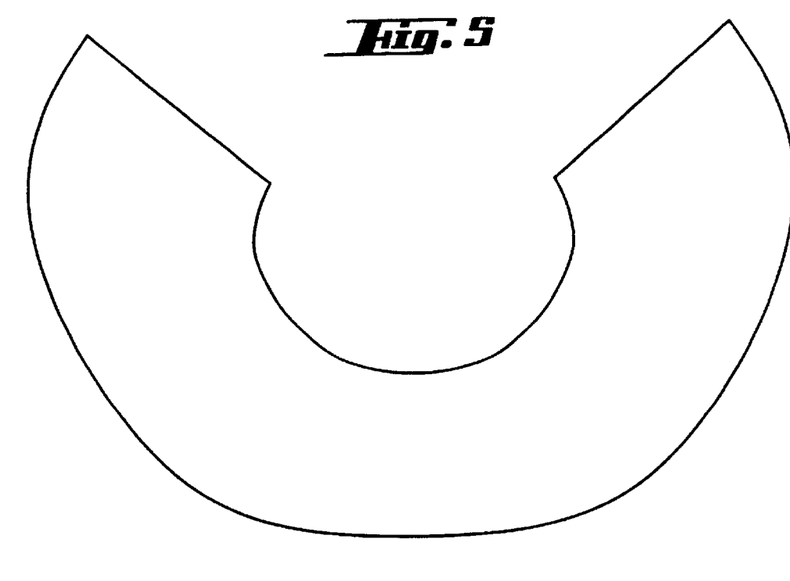
FIG. 5 is a view of the section of material prior to the construction of the bag which forms the wearer facing portion of the bag of a preferred faecal management device in accordance with FIG. 4.

A preferred faecal management device (10) for babies in accordance with FIGS. 4 and 5 has a volume of 700 ml and a maximum span of 17 cm and a C1–C2-distance of 6.6 cm and a maximum width of 7.5 cm.

For bags (11) comprising a wearer facing portion (16) and a garment facing portion (17), where each of said portions comprise separate pieces of material, as depicted in FIGS. 4 and 5, a preferred embodiment of the present invention is characterised by the following features:

The surface area of the wearer facing portion (16) is larger than the surface area of the garment facing portion (17), preferably 5% to 40%, most preferably 10% to 20% larger than the surface area of the garment facing portion (17).

A further feature of such preferred embodiments is that the garment facing portion (17) has a length (L) and a width (I) as defined above, and that the ratio between the length (L) and the width (I) is between 1:0.7 and 0.7:1, more preferably between 1:0.9 and 0.9:1. In one preferred embodiment of the present invention the garment facing portion (17) is of circular shape, said ratio thus being 1:1. In an even more preferred embodiment of the present invention the garment facing portion (17) is of the shape depicted in FIG. 4, where the ratio between the length (L) and the width (I) is 1:0.92.

When a faecal management device (10) is provided with a bag according to the present invention, the bag will be disposed adjacent to the buttocks of the wearer. Thus, the bag (11), more particularly the wearer facing portion (16) of the bag (11), amply covers the buttocks and does not hang between the thighs of the wearer. Consequently the faecal management device (10) can be worn inconspicuously by under garments and can conveniently be combined with a diaper.

Figure 9:
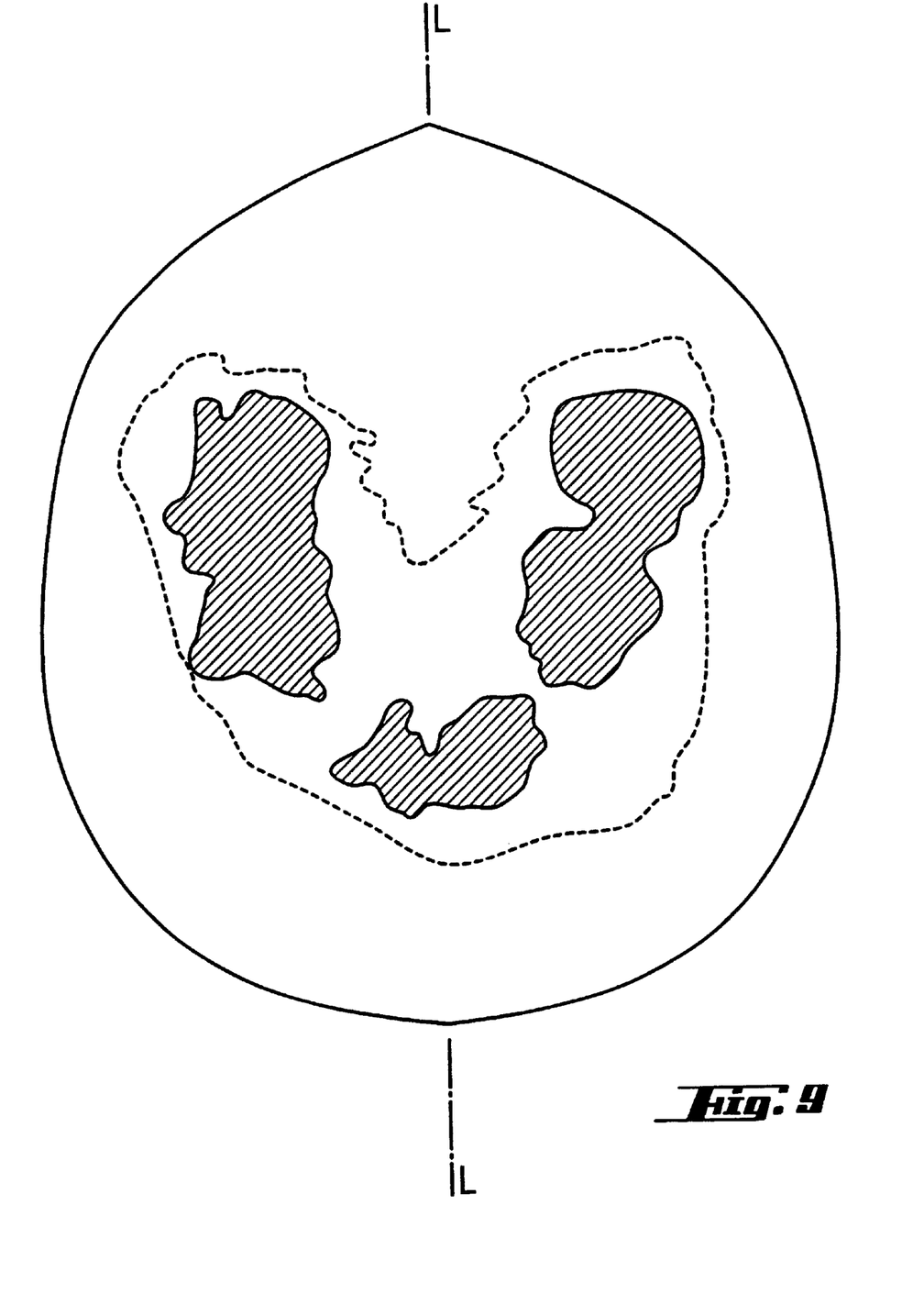
FIG. 9 is an illustration of the areas of the bag (11) which are subject to most pressure by a sitting wearer, taking the example of a baby. The highest pressure areas are denoted by the hatched areas. L denotes the longitudinal direction.

The bag (11) is also preferably designed to provide sufficient volume for faecal material under a variety of wearing conditions, also when worn by a freely moving, i.e., not bedridden wearer. Such wearing conditions include the sitting of the wearer. Sitting on the bag (11) will result in a largely reduced volume in some areas of the bag. Thus, to allow for sitting, the bag (11) is preferably of the appropriate size and shape to provide sufficient volume in areas which are not subjected to much pressure by a sitting wearer. The optimal shape and size will depend on the particular wearer and the design of the faecal management device (10) as a whole. It has been found that sitting on a faecal management device (10) will reduce the volume of the bag (11) available for faecal matter, particularly in certain areas. These areas are those immediately adjacent to the anus of the wearer, but to a lesser degree the areas of the bag adjacent to the genitals, the coccyx and the outer parts of the buttocks, as is illustrated by FIG. 9. Thus it is important to provide sufficient volume in the latter areas.

Preferably, however, the bag (11) is not designed to cover or not to fully cover the genitals of the wearer. This typically improves the wearing comfort of the device (10). Furthermore, when covering the genitals, the faecal management device (10) may hinder the functioning of a diaper, which may be worn in combination in order to absorb urine.

Consequently, the distance ($l_1$) measured in the longitudinal direction from the centre of the aperture (21) to the front end of the bag (11) is preferably shorter than the distance ($l_2$) measured in the longitudinal direction from the centre of the aperture (21) to the rear end of the bag (11), cf. FIG. 7. Thus preferably the bag (11) is asymmetrical to the transversal axis. Most preferably, however, said distance ($l_2$) measured to the rear end of the bag (11) is no more than 50% greater than said distance ($l_1$) measured to said front end. Preferably the aperture (21) is so positioned that the bag (11) is symmetrical to the longitudinal axis.

In choosing the size and shape of the bag (11) of the devices of the present invention, it is also important to consider the exact circumstances of use. For example for devices intended to be utilized if in combination with a diaper, the nature of the diaper itself should be borne in mind to ensure the correct functioning of the device and diaper. For example, disposable diapers as described herein typically have elastically contractible leg cuffs. It is therefore necessary to ensure that the bag is not shaped such that the bag will be entrapped between the wearers' legs and the leg cuffs, as this prevents the intended diaper sealing by the leg cuffs.

Hence a variety of shapes of the bag is within the scope of the present invention. Particularly, preferred shapes are flat circular type bags, cone shaped bags, truncated cone shaped bags and pyramidal or truncated pyramidal shaped bags. In a most preferred embodiment of the present invention, the bag (11) has a substantially truncated cone shape.

In addition, the bag (11) is preferably shaped to allow at least partial insertion and retention of the bag in-between the buttocks of the wearer and thereby ensure good contact between the flange and the skin of the wearer. For example the faecal management bag may be provided with a neck portion or conduit.

What is claimed is:

1. A faecal management device comprising a bag having a longitudinal axis therethrough, said bag having an aperture for the entry of faecal material into said bag and defining an aperture plane, said device further comprising a flange surrounding said aperture, said flange contacting a wearer when said device is in use, said aperture and said flange being bent about said longitudinal axis for registering said bag with the anal opening of a wearer, said bag comprising two pieces of material joined at a seam, a first piece of material juxtaposed with said aperture and diverging outwardly therefrom to said seam and a second piece of material which does not intercept said aperture.

2. A faecal management device according to claim 1 wherein said seam defines a seam plane, said seam plane being substantially parallel to said aperture plane.

3. A faecal management device according to claim 2, wherein said aperture is positioned in a central position in said flange.

4. Faecal management device (10) according to any one of the preceding claims, wherein said bag (11) has a flat circular shape, a cone shape, a truncated cone shape, a pyramidal shape or a truncated pyramidal shape.

* * * * *

UNITED STATES PATENT AND TRADEMARK OFFICE
CERTIFICATE OF CORRECTION

PATENT NO. : 6,398,768 B1  
DATED : June 4, 2002  
INVENTOR(S) : Gianfranco Palumbo et al.

It is certified that error appears in the above-identified patent and that said Letters Patent is hereby corrected as shown below:

Title page,  
[*] Notice: This patent is subject to a terminal disclaimer

Column 4,  
Line 37, "weaning" should read -- wearing --.

Column 5,  
Line 1, "potytetrafluroethylene" should read -- polytetrafluroethylene --.  
Line 2, "meltlow" should read -- melt/low --.

Column 9,  
Line 62, "combiantion" should read -- combination --.  
Line 64, the second occurrence of "that isolates" should be deleted.  
Line 65, "sbsorbent" should read -- absorbent --.

Column 14,  
Line 23, "if" should be deleted.  
Lines 62-63, "any one of the preceding claims" should read -- claim 1 --.

Signed and Sealed this

Fourth Day of February, 2003

JAMES E. ROGAN  
*Director of the United States Patent and Trademark Office*